United States Patent [19]

Dämbkes et al.

[11] Patent Number: 5,072,058

[45] Date of Patent: Dec. 10, 1991

[54] PROCESS FOR THE PREPARATION OF 2,2-DIMETHYLPROPANE-1,3-DIOL

[75] Inventors: Georg Dämbkes; Peter Lappe, both of Dinslaken; Franz Thönnessen; Helmut Springer, both of Oberhausen, all of Fed. Rep. of Germany

[73] Assignee: Hoechst Aktiengesellschaft, Fed. Rep. of Germany

[21] Appl. No.: 632,353

[22] Filed: Dec. 21, 1990

[30] Foreign Application Priority Data

Dec. 23, 1989 [DE] Fed. Rep. of Germany ....... 3942792

[51] Int. Cl.$^5$ ...................... C07C 28/88; C07C 29/14; C07C 31/20
[52] U.S. Cl. .................................... 568/854; 568/853
[58] Field of Search ................................ 568/854, 853

[56] References Cited

U.S. PATENT DOCUMENTS

| | | | |
|---|---|---|---|
| 3,808,280 | 4/1974 | Merger et al. ...................... | 528/853 |
| 4,393,251 | 7/1983 | Bruecker et al. .................... | 568/811 |
| 4,594,461 | 6/1986 | Mager et al. ........................ | 568/853 |
| 4,740,639 | 4/1988 | Beavers ............................... | 568/853 |
| 4,851,592 | 7/1989 | Morris ................................. | 568/853 |
| 4,918,247 | 4/1990 | Breitkopf et al. ................... | 568/854 |

FOREIGN PATENT DOCUMENTS

| | | |
|---|---|---|
| 0142090 | 5/1985 | European Pat. Off. ............ 568/853 |
| 278106 | 12/1987 | European Pat. Off. . |
| 2045668 | 3/1972 | Fed. Rep. of Germany . |
| 2653096 | 5/1978 | Fed. Rep. of Germany . |
| 3638496 | 5/1988 | Fed. Rep. of Germany . |
| 273434 | 11/1989 | German Democratic Rep. . |

*Primary Examiner*—J. E. Evans
*Assistant Examiner*—R. Cook
*Attorney, Agent, or Firm*—Jordan B. Bierman

[57] ABSTRACT

A process for the preparation of 2,2-dimethylpropane-1,3-diol by an addition reaction between isobutyraldehyde and formaldehyde in the presence of tertiary amines as the catalyst, hydrogenation of the reaction mixture, and subsequent distillation. Before the distillation, formaldehyde is added to the hydrogenation product to remove unwanted basic impurities.

20 Claims, No Drawings

PROCESS FOR THE PREPARATION OF 2,2-DIMETHYLPROPANE-1,3-DIOL

This Application claims the priority of German Application P 39 42 792.7, filed Dec. 23, 1990.

The invention relates to a process for the preparation of 2,2-dimethylpropane-1,3-diol from isobutyraldehyde and formaldehyde using tertiary amines as the catalyst, followed by hydrogenation of the reaction mixture and subsequent distillation of the hydrogenation product, after addition of formadehyde.

BACKGROUND OF THE INVENTION

It is known that 2,2-dimethyl-3-hydroxypropanal can be prepared from isobutyraldehyde and formaldehyde by aldol addition and that this hydroxyaldehyde can then be hydrogenated to the corresponding diol. Basic compounds are used as catalysts; alkali metal hydroxides, alkaline earth metal hydroxides, and alkali metal carbonates being commonplace. Amines, in particular tertiary mono- or polyamines such as diamines, have also been used. Such a process is described, for example, in German Patent 19 57 591 B2. To prepare 2,2-dimethylpropane-1,3-diol, isobutyraldehyde and formaldehyde are reacted in the presence of tertiary amines and the reaction mixture obtained is hydrogenated. The following, inter alia, are mentioned as suitable: trimethyl-, triethyl-, methyldiethyl- and methyldiisopropyl- and tributyl amines.

The use of amines as addition catalysts has the advantage that only a minor amount, if any, of by-products which are formed when other basic catalysts are used are formed from isobutyraldehyde and formaldehyde. In contrast, attention must be paid to the complete removal of the amines, because diol contaminated with even only a small amount of amines is unsuitable for many intended uses. The preparation of pure 2,2-dimethylpropane-1,3-diol thus requires a very high separation expenditure.

According to German Patent 36 44 675 Al, it is possible to remove the tertiary amine from the diol completely if tri-n-propylamine is employed as the addition catalyst and the crude product is distilled in the presence of isobutanol. Both primary and secondary amines accompany the tertiary amine from the preparation process or are formed from the tertiary amine used as the catalyst during hydrogenation of the addition product. Moreover, basic products are formed in the course of the reaction by reaction of the primary and secondary amines with isobutyraldehyde and/or formaldehyde. The foregoing products and amines are not removed, or only removed partially, from the reaction mixture.

BRIEF DESCRIPTION OF THE INVENTION

Thus, the object of the present invention is to provide a process which allows reliable and complete removal of the basic components from the 2,2-dimethylpropane-1,3-diol.

According to the invention, this object is achieved by an addition reaction between isobutyraldehyde and formaldehyde in the presence of tertiary amines as the catalyst, hydrogenation of the reaction mixture, and subsequent distillation of the hydrogenation product, the distillation being carried out after addition of formaldehyde. The novel process produces very pure 2,2-dimethylpropane-1,3-diol which contains only amounts of basic conversion products of primary or secondary amines which do not impede further processing of the diol. If it is ensured that the tertiary amine used as the catalyst is also removed completely—or at least almost completely (as by distillation)—a 2,2-dimethylpropane-1,3-diol which can be employed in all the known fields of use is obtained.

DETAILED DESCRIPTION OF THE INVENTION

According to the present process, formaldehyde and isobutyraldehyde are reacted with one another in the first stage. The starting substances can be employed in equimolar ratio, but it is also possible to use one of the two reactants in excess. Formaldehyde is advantageously used as an aqueous solution, the aldehyde content of which is usually about 30% to 49% by weight. The reaction proceeds advantageously at temperatures between 20° and 130° C., and it has been found particularly desirable to carry it out at 80° to 95° C. The reaction generally takes place under normal pressure, but it is also possible to apply increased pressure. Solvents are unnecessary.

Tertiary amines are used as the catalysts. The reaction mixture contains 1 to 20, preferably 2 to 12 mol % of tertiary amines as catalysts, based on the isobutyraldehyde. The process is not tied to the use of a particular tertiary amine; the primary requirement of the amine is that it can be removed as quantitatively as possible from the reaction product by conventional measures. Tri-n-propylamine is particularly desirable as the catalyst because it can be distilled off from the 2,2-dimethylpropane-1,3-diol in a simple manner as an azeotrope with water and i-butanol, as described in German Patent 36 44 675.

In practice, the addition reaction is carried out with stirring in a kettle, or in a reaction tube charged with packing for thorough mixing of the reactants. The reaction proceeds exothermically and can be accelerated by heating. The reaction mixture obtained is subjected to catalytic hydrogenation without prior separation into its constituents or removal of individual components. The addition reaction with hydrogen can be carried out in the gas phase or in the liquid phase. A suitable catalyst is, in particular, supported nickel, which can optionally contain other active metals, such as copper or chromium, as well as activators.

The hydrogenation product can be further processed directly, that is without additional purification. Only if suspended hydrogenation catalysts are used is it advisable to remove the last residues of catalyst by filtration. A typical hydrogenation product has approximately the following composition (the % data in each case is based on the mixture):

| | |
|---|---|
| 2,2-dimethylpropane-1,3-diol | 30% to 74% by weight |
| isobutanol | 20% to 60% by weight |
| tertiary amine | 5% to 15% by weight |
| primary and secondary amine | 0.02% to 0.2% by weight |
| other constituents | 0.1% to 5% by weight |

Compositions of the hydrogenation product which deviate from the above data are possible, depending on the specific procedures of the addition and hydrogenation steps. However, they do not influence the applicability of the novel process.

According to the invention, the hydrogenation product is distilled after addition of formaldehyde. The amount of aldehyde to be added depends on the content of primary and secondary amine in the starting mixture. This content is to be determined analytically, for example by gas chromatography. 2 to 100, preferably 20 to 50 mol of formaldehyde are employed per mol of primary and/or secondary amine. It is advantageously in the form of an aqueous solution containing about 30%-49% by weight of formaldehyde (based on the solution). The methanol which these solutions usually contain for stabilization—in most cases about 1% by weight—does not interfere with their usefulness. Formaldehyde can also be employed as the aqueous solution in polymeric form as paraformaldehyde with equal success.

The formaldehyde is added to the hydrogenation product which has been heated to 40° to 160° C., preferably 55° to 130° C. The reactants are allowed to react for 0.01 to 24 hours, preferably 0.1 to 8 hours and, in particular, 0.5 to 4 hours; it is possible for the reaction to be carried out under normal pressure or under pressure of up to 1 MPa, pressures of 10 to 50 KPa being preferred.

Only minor amounts of primary and secondary amines can be detected in the hydrogenation product treated as described above. The product can be distilled in a known manner under normal or reduced pressure for purification. Continuously operating fractionating columns having 40 to 120, preferably 50 to 70, theoretical plates are usually employed. The column can be equipped with lateral take-offs for removal of the various constituents of the mixture, in particular the tertiary amine and the isobutanol, as well as azeotropes which may form.

The basic compounds formed from the primary and secondary amines distill over together with the tertiary amine employed as the catalyst. This fraction can be recycled to the process, without prior separation into its constituents, and used again as the catalyst.

If tri-n-propylamine is used as the catalyst, the distillation can be carried out in a column provided with two lateral take-offs. Tri-n-propylamine, residual amounts of isobutanol, and the basic impurities are removed at the lower lateral take-off. A two-phase system, the organic phase of which consists chiefly of isobutanol, is stripped off at the upper lateral take-off. Methanol is obtained at the top of the column and is diverted together with low-boiling by-products. The water of the reaction and the remainder of the methanol are removed via the aqueous phase at the upper lateral take-off.

The novel process is illustrated in more detail by the following examples.

Examples

A mixture having the composition

| 2,2-dimethylpropane-1,3-diol | 36.0% by weight |
| --- | --- |
| isobutanol | 54.4% by weight |
| tri-n-propylamine | 7.88% by weight |
| mono- and di-n-propylamine | 0.04% by weight |
| other constituents | 1.68% by weight | was used in the following Examples. It was obtained by hydrogenation of the addition product of formaldehyde and isobutyraldehyde in isobutanol as the solvent and in the presence of tri-n-propylamine as the catalyst.

Different amounts of formalin were added to the product to remove the mono- and di-n-propylamine. The results of the investigations are summarized in the following Table:

| Mol of HCHO per (37% strength) Mol of MnPA/DnPA* | Temperature (°C.) | Time (h) | Pressure (MPa) | Gas chromatography analysis of MnPA/DnPA* (%) |
| --- | --- | --- | --- | --- |
| 15 | 94 | 1 | — | 0.001 |
| 10 | 94 | 1 | — | 0.002 |
| 5 | 94 | 1 | — | 0.018 |
| 3 | 94 | 1 | — | 0.023 |
| 10 | 130 | 1 | 0.32 | 0.001 |
| 5 | 130 | 1 | 0.32 | 0.02 |

The purified 2,2-dimethylpropane-1,3-diol had an alkalinity of less than 5 ppm N.

What we claim is:

1. A process for the purification of 2,2-dimethyl-propane-1,3-diol which is a hydrogenation product of a reaction product of an addition reaction between isobutyraldehyde and reaction formaldehyde in the presence of at least one tertiary amine as a catalyst, said process comprising introduction of an amount of added formaldehyde into said hydrogenation product to permit a post reaction followed by distillation.

2. The process of claim 1 wherein said amount is 2 to 100 mols of said added formaldehyde per mol of primary and/or secondary amine in said hydrogenation product.

3. The process of claim 2 wherein said amount is 20 to 50 mols.

4. The process of claim 1 wherein said added formaldehyde is an aqueous solution or paraformaldehyde.

5. The process of claim 1 wherein, after said addition, said hydrogenation product is heated to a post reaction temperature of 40° to 160° C.

6. The process of claim 5 wherein said post reaction temperature is 55° to 130° C.

7. The process of claim 1 wherein said post reaction takes place for a period of 0.01 to 24 hours.

8. The process of claim 7 wherein said period is 0.1 to 8 hours.

9. The process of claim 8 wherein said period is 0.5 to 4 hours.

10. The process of claim 1 wherein said catalyst is tri-n-propylamine.

11. The process of claim 1 wherein said distillation is in a column having 40 to 120 theoretical plates.

12. The process of claim 11 wherein said column has 50 to 70 theoretical plates.

13. The process of claim 10 wherein at least one substance selected from the group consisting of said tri-n-propyl amine, residual isobutanol, and basic impurities is withdrawn through a lower lateral take-off.

14. The process of claim 10 wherein a two phase system is formed and is withdrawn through an upper lateral take-off.

15. The process of claim 13 wherein a system having an aqueous phase and an organic phase is formed and stripped off through an upper lateral take-off, said organic phase comprising primarily isobutanol, said aqueous phase comprising water of reaction and methanol.

16. The process of claim 1 wherein said addition reaction is carried out at 20° to 130° C.

17. The process of claim 16 wherein said addition reaction is carried out at 80° to 95° C.

18. A process for the preparation of 2,2-dimethylpropane-1,3-diol comprising an addition reaction between isobutyraldehyde and reaction formaldehyde in the presence of at least one tertiary amine as a catalyst to form a reaction product, hydrogenation of said reaction product to form a hydrogenation product, introduction of added formaldehyde into said hydrogenation product to form a mixture and permit a post reaction, and distillation of said mixture.

19. The process of claim 18 wherein 2 to 100 mols of said added formaldehyde per mol of primary and/or secondary amine in said hydrogenation product are in said mixture.

20. The process of claim 18 wherein said post reaction is at a temperature of 40° to 160° C.

* * * * *